(12) United States Patent
Hahn et al.

(10) Patent No.: US 10,010,664 B2
(45) Date of Patent: Jul. 3, 2018

(54) LIFE SUPPORT SYSTEM

(75) Inventors: Andreas Hahn, Berg (DE); Erwin Knott, Poing (DE)

(73) Assignee: Sorin Group Deutschland GmbH, München (DE)

( * ) Notice: Subject to any disclaimer, the term of this patent is extended or adjusted under 35 U.S.C. 154(b) by 776 days.

(21) Appl. No.: 12/995,118

(22) PCT Filed: May 29, 2008

(86) PCT No.: PCT/EP2008/056600
§ 371 (c)(1),
(2), (4) Date: Mar. 2, 2011

(87) PCT Pub. No.: WO2009/143890
PCT Pub. Date: Dec. 3, 2009

(65) Prior Publication Data
US 2011/0144556 A1    Jun. 16, 2011

(51) Int. Cl.
  A61M 37/00   (2006.01)
  A61M 1/36    (2006.01)
  A61M 31/00   (2006.01)
  A61B 5/00    (2006.01)

(52) U.S. Cl.
  CPC ... A61M 1/3621 (2013.01); *A47B 2200/0078* (2013.01); *A61B 5/00* (2013.01); *A61M 1/3664* (2013.01); *A61M 1/3666* (2013.01); *A61M 2205/502* (2013.01); *A61M 2209/08* (2013.01)

(58) Field of Classification Search
  CPC ......... G06F 19/3406; A47B 2200/0078; A61B 5/00; A61M 1/3666
  USPC ................. 604/4.01, 6.14; 600/301; 312/198
  See application file for complete search history.

(56) References Cited

U.S. PATENT DOCUMENTS

| | | | |
|---|---|---|---|
| 4,012,088 A * | 3/1977 | Platz | 312/198 |
| 5,573,502 A * | 11/1996 | LeCocq et al. | 604/4.01 |
| 5,622,429 A | 4/1997 | Heinze | |
| 5,702,358 A | 12/1997 | Witherspoon et al. | |
| 6,071,258 A | 6/2000 | Dalke et al. | |

(Continued)

FOREIGN PATENT DOCUMENTS

| | | | |
|---|---|---|---|
| EP | 0 882 462 B1 | 1/2004 | |
| EP | 1 767 232 B1 | 12/2008 | |

(Continued)

OTHER PUBLICATIONS

International Preliminary Report on Patentability issued in PCT/EP2008/056600, completed Sep. 17, 2009 (with English Translation).

(Continued)

*Primary Examiner* — Tatyana Zalukaeva
*Assistant Examiner* — Andew J Mensh
(74) *Attorney, Agent, or Firm* — Faegre Baker Daniels LLP

(57) ABSTRACT

A life support system such as a heart-lung machine may include a plurality of medical devices a control panel and an excellent control position. The control panel may have separate control elements for operating the medical devices. The control panel may be constructed protruding essentially flat over a floor area of the majority of the medical devices. The control panel may be constructed to protrude in such a manner, that a control element, aligned only with a particular device and with the control position, is assigned to each device.

18 Claims, 3 Drawing Sheets

(56) References Cited

U.S. PATENT DOCUMENTS

| | | | |
|---|---|---|---|
| 6,234,172 B1 * | 5/2001 | Ausbourne et al. ......... | 128/845 |
| 8,038,593 B2 * | 10/2011 | Friedman et al. ............. | 600/26 |
| 2002/0085952 A1 * | 7/2002 | Ellingboe et al. ............. | 422/45 |

FOREIGN PATENT DOCUMENTS

| | | |
|---|---|---|
| JP | 3041846 U | 7/1997 |
| JP | 9512202 A | 12/1997 |
| JP | 2000140093 A | 5/2000 |
| WO | 96 25972 | 8/1996 |

OTHER PUBLICATIONS

Written Opinion issued in PCT/EP2008/056600, dated Jun. 10, 2009.

USH1324H—United States Statutory Invention Registration, Published Jun. 7, 1994, Dalke et al.

International Search Report of PCT/EP2008/056600, dated Mar. 10, 2009, 10 pages.

* cited by examiner

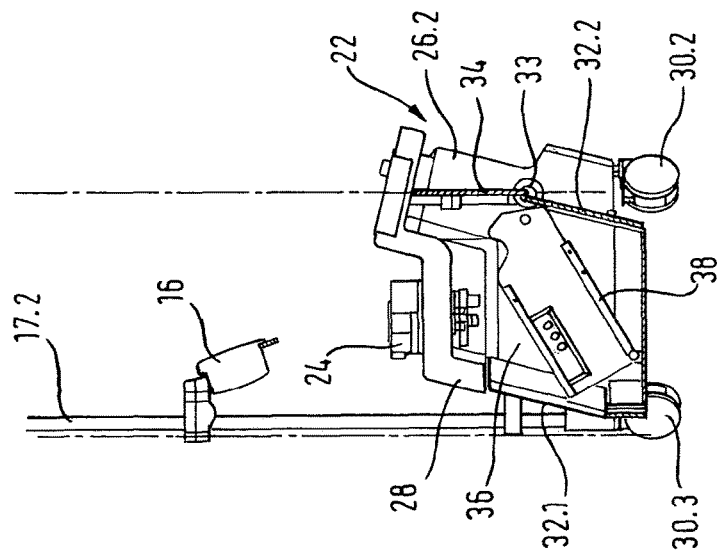
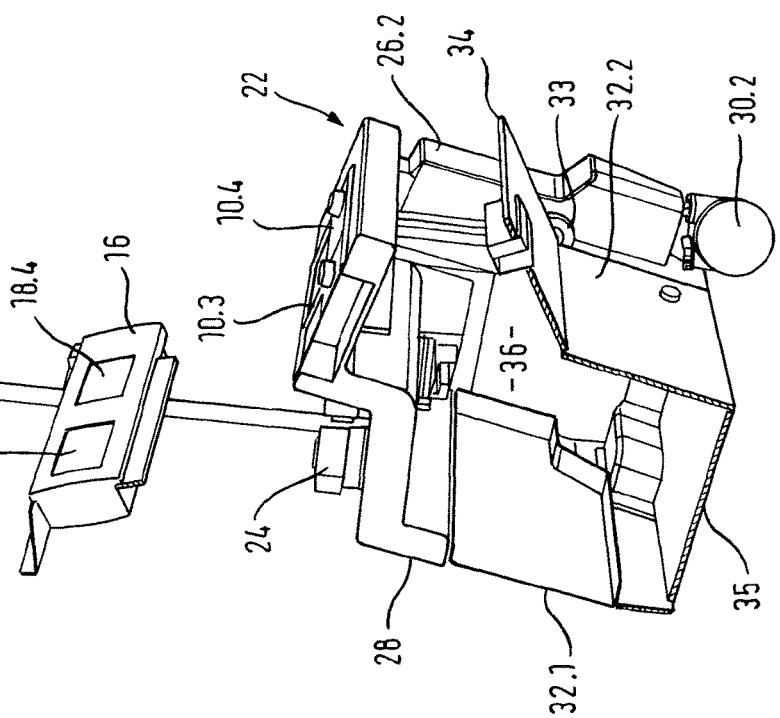

LIFE SUPPORT SYSTEM

CROSS-REFERENCE TO RELATED APPLICATIONS

The present application is a national phase application, filed pursuant to 35 U.S.C. § 371, of PCT/EP2008/056600 that was filed May 29, 2008, said application being incorporated herein by reference in its entirety.

FIELD OF THE INVENTION

The invention relates to a life support system, particularly to a heart-lung machine which comprises a plurality of medical devices, a control panel and a control position, wherein the control panel has separate control elements for operating the medical devices. Further, the invention relates to a medical device aggregate such as a life support system which comprises one or more medical devices, two lateral members that extend substantially vertically, and a connection member that extends between the lateral members and preferably substantially horizontally.

PRIOR ART

In healthcare, life support systems, in particular heart-lung machines are used to support or also substitute vital body functions such as circulation. Life support systems have been known for decades and were constantly developed and improved in the past. For example, the heart-lung machine has been designed in various ways by adding components such as blood pumps, oxygenators, heat exchangers, control elements, power supplies, mounting elements etc., and by arranging them in different ways. The various designs had the object to position the components efficiently and to make the life support system easy to use at the same time. As regards universal deployability such life support systems increasingly came to the fore, which comprise a plurality of medical devices. Consequently, with an increasing number of devices, a largely intuitive and thus error-proof operability of such a life support system has gained increasing importance. Due to the multiplicity of medical devices and of the associated control elements and peripherals, and in consideration of the concurrent restriction on volume of the device aggregate, operability becomes an important criterion in the construction of life support systems.

In order to fulfill this requirement, DE 197 23 671 A1 describes a heart-lung machine having more than two blood pumps, in which a special arrangement of the blood pumps serves for easy operability of the heart-lung machine. For example, it is described therein that the blood pumps are not arranged in a row next to each other but around the oxygenator or heat exchanger. This allows a heart-lung machine having a design as compact as possible.

However, there is still the problem of clear arrangement in a life support system with a plurality of medical devices, and thus one cannot exclude an operating error which during use of the life support system might have fatal consequences.

Moreover, in the design of devices for professional use aspects of occupational health should be given greater consideration, too. This aims to largely avoid the occurrence of postural deformities or other health problems that can be ascribed to continuous use of a professionally utilized device on part of the operating personnel. As a result of this requirement, when constructing a device for professional use, it is of increased importance that the operation of the device is not only as intuitive as possible but also user-friendly in the sense of an ergonomic design.

In present life support systems, this aspect has been almost completely ignored, and poses a further challenge regarding the structure of a life support system.

SUMMARY OF THE INVENTION

It is an object of the invention to design a device aggregate belonging to the technical field, which improves operability of known devices without having increased space requirements.

The object is achieved by means of the features of claims 1 and 11. Thus, according to the invention the life support system is on the one hand characterized in that the control panel is constructed protruding essentially flat over the base area of the plurality of medical devices in such a manner that to each device a control element aligned only with this device and with the control position is assigned. The base area (footprint) of the plurality of medical devices is to be regarded without the base area (footprint) of the control panel, thus being able to describe the two-dimensionally extended control panel as protruding over this base area. Each device is operated by a control element arranged in alignment with this device and the control position. The control element may also be a control module comprising a plurality of single control elements, wherein the control module serves mainly, and in particular exclusively for the operation the device arranged in alignment therewith and with the control position. Control elements for the operation of more than one device may also be included in a control module. Examples for control modules and control elements are rotary or sliding controls, switches, push button or touch screens. The alignments of the plurality of medical devices thus substantially converge in the control position.

By the inventive configuration of the life support system and the alignment of the control elements on the control panel with the medical devices starting from the allocated control position an intuitive correlation of the control element and the controlled device is ensured. Although the life support system can be operated from different positions, an allocated control position is defined by the inventive structure of the life support system, in particular by an intersection of the alignments.

Advantageously, the control elements are arranged next to each other on the control panel and are preferably in a substantially horizontal alignment with the control position. An arrangement of the control elements next to each other on the control panel may be effected both in a linear sequence and in a half-circular shape or a similar slightly bent arrangement. The fact that the control position and the control elements and the associated devices are to be in a substantially horizontal alignment means that each projection of a control element or a medical device into a horizontal plane comprising also the control position is substantially arranged in alignment. Height differences in a vertical direction between the medical devices and the associated control elements or the control position are not to be considered here. In a particularly positive manner the arrangement of the control elements next to each other on the control panel allows for a modular configuration of the life support system, in which a plurality of medical devices and corresponding control elements can thus be inserted into the system and removed from it.

Advantageously, the horizontal alignments of the control position with the control elements and the medical devices of the plurality radially converge in the control position. In this preferred embodiment, the control elements and the corresponding medical devices are therefore arranged in radial coordination with the control position. Alternatively, it also possible to arrange the control elements and the corresponding devices in such alignment that the alignments do not intersect or do not intersect in the control position but, for example, in a region behind the control position. It is also possible that the control elements and the medical devices are linearly arranged next to each other so that their alignments run substantially in parallel through the area of the allocated control position.

In the preferred embodiment, in which the horizontal alignments of the control position with the control elements and the medical devices of the plurality radially converge in the control position, a particularly positive and intuitive association of the control elements with the medical devices is ensured. This is particularly true because an operator standing at the control position always looks in the direction of the alignment between the control position, the control element and the corresponding medical device.

Preferably, the control elements are arranged in a predeterminable distance interval from the control position. In such an arrangement it is for example possible to provide, as distance interval, a grasping region of an operator standing at the control position.

Advantageously, the life support system further comprises at display panel having separate display and/or monitoring elements that are preferably firmly built into the display panel, of which each display and/or monitoring element serves for displaying or monitoring system and/or operating conditions of an associated medical device. Due to the display and/or monitoring elements in the display panel, a speedy testing of the functions of the medical devices is ensured. Through the display and/or monitoring elements an operator may always check if the medical devices work as desired. The display and/or monitoring elements may be both firmly built into the display panel and be removable from the display panel. Examples for display and/or monitoring elements are CRT or TFT monitors or touch screens. The displayed and/or monitored operating conditions may be pump conditions, stop watches, target values for different parameters of the pump or the patient status, a battery and battery charge condition or other data relevant for the operation of the life support system.

Here, it is particularly preferred that a control element, a medical device and a display and/or monitoring element are arranged in substantial alignment with the control position. In this manner it is thus possible to have both the control element and the display and/or monitoring element in alignment with the corresponding medical device. This arrangement allows for a direct and intuitive association of the elements of a medical device with the medical device itself. Thus, seen from the control position, the control element, the display and/or monitoring element and the medical device or their projections into a horizontal plane are arranged substantially on a straight line. Therefore, an operator at the control position may infer merely from the position of a control element or a display and/or a monitoring element that it belongs to a certain medical device of the life support system. A clear and error-proof labeling of the corresponding elements of a medical device will thus have to be present at most in support of the association between the individual medical devices and the corresponding control elements and display and/or monitoring elements.

Advantageously, each of the display and/or monitoring elements are arranged below the control elements of the medical devices, seen from the control position. Such an arrangement ensures that the display and/or monitoring elements can always be easily read out from the control position.

Further, the display and/or monitoring elements, the medical devices and the control elements, as seen from the control position, are advantageously arranged in this order at successive polar angles. The polar angle conventionally denotes an angle with respect to a vertically oriented polar axis. Seen from a point of observation at the control position, the display and/or monitoring element thus lies "above" the medical device, and the latter lies "above" the control element, wherein "above" does not denote a relative vertical position with respect to the single elements, but describes the inclination of a line of sight (viewing region) with respect to a horizontal plane. The sequence of said display and/or monitoring elements, medical devices and control elements may also be inverted so as to arrange the display and/or monitoring element "below" the medical devices, and the latter "below" the control elements, as seen from the control position. The different polar angles at which the display and/or monitoring elements, the medical devices and the control elements are arranged, as seen from the control position, may come about both by an actual vertical spacing and by a horizontal spacing at different distances from the control position. This arrangement may also be achieved if the control elements, as seen from the control position, are arranged in front of the medical devices, and the latter are arranged below the display and/or monitoring elements each in horizontal alignment with the control position.

It is particularly preferred to arrange a control element, a medical device and a display and/or monitoring element each on an ergonomical radius. The arrangement on an ergonomical radius ensures that the control element, the medical device and the display and/or monitoring element are each reachable from the control position. Depending upon a vertical height with respect to the control position, a horizontal spacing from the control position is adopted, which is reached by a user standing at the corresponding height in the control position. The horizontal spacing is largest at an arm's height of an operator standing at the control position, and progressively decreases in an upward and downward direction.

Most preferably the life support system is characterized in that the control panel protrudes across the base area of the plurality of medical devices above the knee height of an operator sitting at the control position, in that further the distance of the control elements to the control position is within reach of the operator and the display and/or monitoring elements are positionable at an eye level of the operator. By means of such a configuration of the life support system it can be ensured that an intuitive and ergonomically pleasant operation of the life support system is possible. An operator sitting at the control position, the knee height of which is substantially constant irrespective of body height and above which knee height the control panel protrudes across the base area of the plurality of medical devices, may thus comfortably reach the control elements on the control panel when sitting and intuitively operate the medical devices that are arranged in alignment with the control elements. The fact that the distance of the control elements to the control position is within reach of the operator additionally renders operation of the control elements more pleasant. Reading out the display and/or monitoring elements that are positionable at eye level of the operator is particularly comfortable at the eye level of the operator. Thus, a life support system is provided which allows an intuitive and, thus, particularly error-free operation of a life support system while at the same time ergonomically configuring this life support system. Apart from the error-free operability due to the intuitive arrangement of the devices, a high occupational health standard is made possible due to the ergonomic configuration of the life support system.

According to the invention, a medical device aggregate, in particular a life support system such as a heart-lung machine, and having one or more medical devices, two lateral members extending substantially vertically and a connection member extending between the lateral members and preferably substantially horizontally, is on the other hand characterized in that the connection member connects the lateral members to each other in a dimensionally stable manner, and that the connection member and the lateral members form a frame for supporting the medical device or the medical devices so as to allow the medical device or the medical devices to be received at least partially between the lateral members. In this context, dimensionally stable means at least that the lateral members are fastened in relation to each other in a stationary manner and in fixed orientation by the connection member. In particular, by the inventive configuration of a medical device aggregate a life support system can be provided in which the single elements can be positioned intuitively and ergonomically in the above sense. Configuring the medical device aggregate to have a frame for supporting the medical device or the medical devices and which is formed by the connection member and the lateral members so as to receive the medical device or the medical devices at least partially between the lateral members constitutes a design of a medical device aggregate, in particular a life support system such as a heart-lung machine, differing from the state of the art. In the hitherto common configuration of a medical device aggregate elements such as medical devices, control elements or display and/or monitoring elements as well as peripherals are positioned on a common support. Therefore, according to the present invention at least parts of the medical devices included in the medical device aggregate or peripheral devices necessary therefor, may be received between the lateral members.

Preferably, at least one of the lateral members extends flat. By such a configuration of the lateral members, they may not only be made particularly robust, but they also provide good protection in a lateral direction for the parts of the device aggregate received between the lateral members.

Alternatively, one or more of the lateral members may also be rod-shaped.

In a further preferred embodiment, the lateral members are supported on rollers, and force components acting vertically upon them are discharged via the rollers. In this manner, the medical device aggregate is given the capability to be moved for example between different operating theaters within a hospital, to individual patients in intensive care units or in patient rooms. The lateral members are configured so as to discharge the force components acting vertically upon them via the rollers. To that end, not every lateral members must be supported on rollers. For example, it is also possible that in the case of two lateral members only one lateral member is supported on rollers and the other is not designed to roll. In this case, the lateral member not capable to roll can for example be lifted and the device aggregate can be displaced on the rollers of the remaining lateral member. Discharging the force via the lateral members, in conjunction with forming a frame, makes the medical device aggregate particularly suitable as mobile device aggregate.

Preferably, the lateral members and the connection member define a substantially closed space. This means that the lateral members and the connection member are delimiting surfaces of this closed space. Between the lateral members and the connection member, that is in the substantially closed space, different medical devices, power supply appliances such as a battery, electronic elements or cable and/or hose connections can be stored, which consequently do not obstruct mobility.

Advantageously, a cover that extends substantially flat and vertically and that might be made of sheet metal, is mounted between two of the lateral members. The cover thus forms vertical walls, for example. The cover offers protection for the parts of the medical devices housed between the lateral members and directs the attention of the operator to the essential control elements by accommodating parts such as the battery, slots for printed circuit boards or cables and hose connections, parts which are necessary for operation but irrelevant for control, behind the cover and, thus, out of the line of sight of an operator or a patient. The cover may be made of sheet metal as well as of other materials.

Advantageously, the cover encloses the space in the direction of a horizontal plane and, preferably, comprises an openable flap. In such a configuration of the medical device aggregate the cover, which for example is constituted by two plates at a front and back side between the exemplary flat lateral members, defines a largely closed volume in the space between the lateral members. An upper delimitation of this volume between the lateral members and the cover may also be provided by such a cover, but is preferably occupied by one or more connection members as well as the medical devices and/or the control elements, for example. A lower delimitation of the volume may be given by a further cover, however the volume may remain open also towards the bottom, for example for cooling purposes. Due to the presence of an openable flap pointing to a front and/or rear side of the medical device aggregate, for example, it is possible to reach from the outside the parts of the medical devices present in the volume between the lateral members and the cover, such as printed circuit boards, cables and/or hose connections or a power supply provided therein. Thus, particularly easy maintenance of the medical device aggregate is ensured. The medical or peripheral devices accommodated in the volume are, thus, covered in everyday operation but are nevertheless easily accessible, for example for maintenance purposes.

Within said space, the medical device aggregate preferably comprises an interface element for connecting the medical device or the medical devices, wherein the interface element is held by a lateral member and preferably comprises a plurality of slots for electronic circuit boards. Due to its central position, the space between the lateral members is particularly suitable for centrally accommodating important electronic components therein. In addition, the space between the lateral members is closable, for example by means of a cover, so that the electronic components present there are both protected from outer influences and are hidden.

Preferably, the lateral members and the connection member are made by aluminium die casting, in particular in one piece. The lateral members and the connection member which may also comprise two or more connections between the lateral members, form a torsional box which ensures the strength of the medical device aggregate.

The above-described structure of the medical device aggregate allows cable connections between individual medical devices, which are arranged in the upper region of the device aggregate, to run in the upper part of the torsional box. Thus, due to the cable connections running through the upper part and due to the box shape of the device aggregate, easy access for purposes of maintenance, set up and battery exchange is made possible. Moreover, the above-described device aggregate is preferably enhancable by a pole extension system. Apart from being designed in one piece with the connection part, the lateral parts may also be screwed to the connection part. In the above-described device aggregate, the lateral parts form supports between which there is a large volume, for example for accommodating the electronics, such as a circuit board or a plug-in board, as described above. As the stability of the device aggregate is ensured by the lateral parts and the connection part inbetween, it is additionally possible to provide between the lateral parts also space for the knees of an operator sitting at a control position, for example. The circuit board and plug-in boards are preferably obliquely installed in the volume between the lateral parts in order to create space for the knees. It is also possible that the medical or peripheral devices in the above-described device aggregate may be utilized in a modular manner and are exchangeable. In particular, this may be also realized by a plug-in system of the electronic devices, by means of which a proper connection of the respective electric and electronic contacts is ensured. Since the lateral members are suitable as supports, no further brackets are necessary for a secure support of the medical device aggregate. In particular, vertical forces can be discharged directly via the lateral members.

As regards the inventive life support system, a display and/or monitoring element may have a variable height. In particular, this may be achieved by mounting the display and/or monitoring element on one or more vertically arranged poles. Advantageously, the display and/or monitoring elements are tilted around a horizontal axis so as to enable a user sitting at the control position to comfortably look at these elements and read them out. Since the height of the lower leg of an adult operator is largely invariable, the height of the control panel which is constructed protruding essentially flat over the base area of the plurality of medical devices, may be designed to be fixed. This facilitates the structure of the life support system and reduces production costs. Preferably, the distance between the eye of an operator and the display and/or monitoring element may additionally be adjusted, and due to the possibility to get below the substantially flat control panel, the distance between the trunk of the operator and the control elements of the medical devices is adjustable. The height of the control panel preferably corresponds to an elbow height of a sitting operator, and the width of the control panel is preferably limited. A preferred maximum width of the control panel is 70 cm. In particular, an ergonomic chair is suitable for an ergonomic positioning of the operator, in particular for a proper seat height and trunk inclination.

Further preferred are the following embodiments:

1. Module carrier for carrying at least two device modules of a medical device aggregate, comprising two lateral members that extend substantially vertically and a connection member, characterized in that the connection member fastens the lateral members to each other so as to define a space substantially delimited by the lateral members for the at least partial introduction of device modules and/or support devices of the device aggregate.

2. Module carrier according to embodiment 1, characterized in that at least one of the lateral members extends flat and forms a side surface of the space.

3. Module carrier according to embodiment 1 or 2, characterized in that the connection member forms a dimensionally stable connection between the lateral members.

4. Module carrier according to one of the embodiments 1 to 3, characterized in that the lateral members are supported on rollers and discharge force components acting upon them via the rollers.

5. Module carrier according to one of the embodiments 1 to 4, characterized in that a cover extending substantially flat and vertically is installed between the lateral members.

6. Module carrier according to embodiment 5, characterized in that the cover encloses the space in the direction of a horizontal plane and comprises an openable flap.

7. Module carrier according to one of the embodiments 1 to 6, characterized by a holding element for modularly holding device components, wherein the holding element is supported by a lateral member.

8. Module carrier according to embodiment 7, characterized in that the holding element is arranged at least partially in the space.

9. Module carrier according to embodiment 7 or 8, characterized in that the holding element comprises a plurality of slots for electronic plug-in boards.

10. Module carrier according to one of the embodiments 1 to 9, characterized in that a control aggregate having separate control modules for operating the respective device modules is provided between the lateral members.

11. Module support according to embodiment 10, characterized in that the control aggregate substantially forms a surface protruding between the lateral members.

12. Module carrier according to embodiment 10 or 11, characterized in that in the control aggregate the respective control modules for operating the device modules are arranged next to each other.

13. Module carrier according to one of the embodiments 10 to 12, and comprising a control position, characterized in that the control modules are located in a predeterminable spacing interval, as seen from the control position.

14. Module carrier according to one of the embodiments 10 to 13, characterized in that it further comprises a display aggregate having separate display and/or monitoring modules for displaying and/or monitoring system and/or operating conditions of the respective device modules.

15. Module carrier according to the embodiments 13 and 14, characterized in that at the control position, the respective control module and the respective display and/or monitoring module of a device module are arranged in alignment.

16. Module carrier according to embodiment 15, characterized in that the display and/or monitoring modules, as seen from the control position, are respectively arranged above the control modules of the device modules on an ergonomical radius of the control position.

Further preferred embodiments will be described by means of the following detailed description of the drawings and the claims.

BRIEF DESCRIPTION OF THE DRAWINGS

FIG. 5 is a sectional perspective view of the medical device aggregate of FIG. 4;
and FIG. 6 shows a side view of the medical device aggregate of FIGS. 4 and 5 in a sectional representation.

PREFERRED EMBODIMENTS

Figure 1:
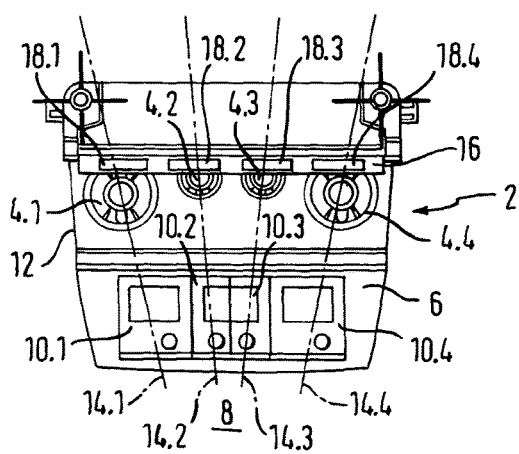
FIG. 1 shows a top view of a life support system.

FIG. 1 shows a top view of a life support system, that is a heart-lung machine 2. In the lower part of FIG. 1 four control elements 10.1 to 10.4 are shown, which are linearly arranged next to each other on a control panel 6 of the heart-lung machine 2. Each of the control elements 10.1 to 10.4 comprises a rotary switch and an input and/or display element.

Above the control panel 6 with the control elements 10.1 to 10.4 there is a region in which four medical pumps 4.1 to 4.4 are arranged. The medical pumps 4.1 to 4.4 form a plurality of medical devices and are also arranged substantially linearly next to each other. The arrangement of the pumps 4.1 to 4.4 as well as of their necessary peripheral devices such as electronic controls or a battery, defines a base area 12 in which the plurality of medical devices is arranged. It can be clearly seen from FIG. 1 that the control panel 6 with the control elements 10.1 to 10.4 protrudes flat over the base area 12 in the direction of the lower edge of FIG. 1.

It can be seen that alignments 14.1 to 14.4, on each of which a pump 4.1 to 4.4 and an associated control element 10.1 to 10.4 is located, converge in a denoted control position 8. The convergence of the alignments 14.1 to 14.4 distinguishes the control position 8 from other possible positions from which the medical device may also be operated. FIG. 1 clearly shows how the respective alignments 14.1 to 14.4 between the pumps 4.1 to 4.4 and the associated control elements 10.1 to 10.4 converge fan-like in a control position 8. The designated control position 8, in which the alignments 14.1 to 14.4 converge, is the preferred location of an operator of the medical device during operation of the medical device.

Further, in the upper region of the drawing, FIG. 1 shows a display panel 16 in which four monitors 18.1 to 18.4 are embedded. The monitors 18.1 to 18.4 are also located on the respective alignments 14.1 to 14.4. That is, a control element 10.1 to 10.4, the associated pump 4.1 to 4.4 as well as the associated monitor 18.1 to 18.4 are each located on an alignment 14.1 to 14.4.

Figure 2:
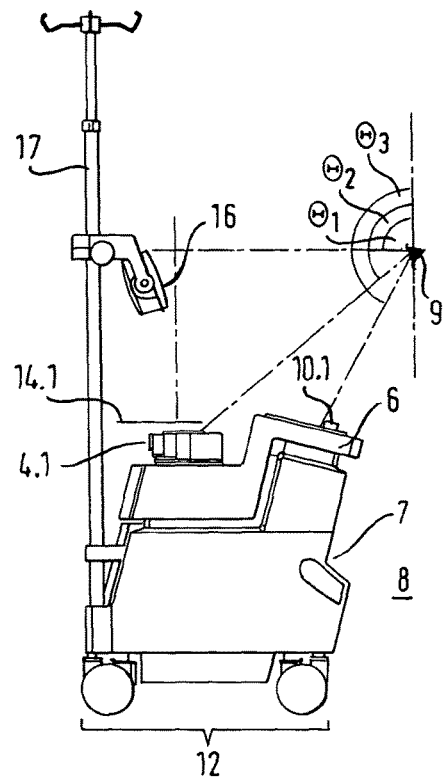
FIG. 2 shows a side view of the life support system of FIG. 1.

FIG. 2 shows a side view of the heart-lung machine 2 of FIG. 1. Apart from the elements described already in FIG. 1, FIG. 2 shows a pole system 17 on which the display panel 16 is mounted. The display panel 16 is located substantially vertically above the pumps 4.1 to 4.4, of which only pump 4.1 is visible in FIG. 2, and may be continuously adjusted in its height along the pole system 17. The height of the display panel 16 is adjusted in conformity with the body dimensions of an operator present in the control position 8.

FIG. 2 clearly shows that the control panel 6 is constructed to protrude flat over the base area 12 of the plurality of medical devices 4.1 to 4.4. Further, it can be taken from FIG. 2 that the display panel 16, the pump 4.1 and the control element 10.1 on the control panel 6, seen from the point of observation 9 of an operator present at the control position 8, are arranged at successive polar angles $\theta_1$ to $\theta_3$. Here, the display panel 16 is substantially located at the same height as the observation point 9. The polar angle $\theta_1$ between the line of sight from the point of observation 9 to the display panel 16 and the vertically upward-pointing polar axis is thus about 90° here. Below that, at a slightly larger polar angle $\theta_2$, the pump 4.1 is located, followed by the control element 10.1 on the control panel 6 at a still larger polar angle $\theta_3$. FIG. 2 shows that the actual height of the control element 10.1 is above the height of the pump 4.1. Nevertheless, the polar angle $\theta_3$ at which an operator at the point of observation 9 looks at the control element 10.1, is larger than the polar angle $\theta_2$ at which the operator looks at the pump 4.1 from the point of observation 9. The pump 4.1 is arranged behind the control element 10.1, as seen from the control position 8.

The just described correlations between the control element 10.1, the pump 4.1 and the display panel 16, in which inter alia the monitor 18.1 is located, analogously apply to the remaining control elements 10.2 to 10.4, the pumps 4.2 to 4.4 and the display panel 16 having the remaining monitors 18.2 to 18.4.

The side view in FIG. 2 additionally shows a recess 7 that can accommodate the knees of an operator sitting at the control position 8 so as to allow the operator to both sit at the control position 8 and be close to the control elements 10.1 to 10.4.

Figure 3:
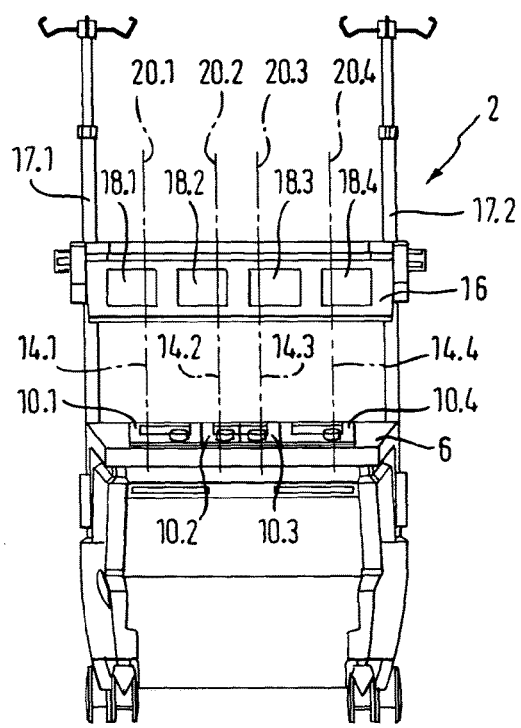
FIG. 3 shows a front view of the life support system of FIGS. 1 and 2.

FIG. 3 shows a front view of the heart-lung machine 2 shown in FIGS. 1 and 2. In the center region of the drawing, the control elements 10.1 to 10.4 are shown arranged on the control panel 6. Starting at the control position 8, the view from which is largely illustrated by FIG. 3, the alignments 14.1 to 14.4 run across the control elements 10.1 to 10.4, the pumps 4.1 to 4.4 (not shown) and the monitors 18.1 to 18.4 in the display panel 16 as display and/or monitoring elements that are, in the embodiment shown in FIG. 3, provided for example by touch screen monitors. The front view of the heart-lung machine 2 shows that the pole system 17 of FIG. 2 is formed by two poles 17.1, 17.2, which mounts the display panel 16 and, thus, the monitors 18.1 to 18.4 with their vertical position being continuously adjustable.

Moreover, FIG. 3 indicates that the control elements 10.1 to 10.4, the pumps 4.1 to 4.4 (not shown) and the monitors 18.1 to 18.4 are located on ergonomic radii 20.1 to 20.4, wherein each ergonomic radius 20.1 to 20.4 is located together with the respective alignment 14.1 to 14.4 in a vertical plane, respectively. It can also be seen that the control elements 10.1 to 10.4, the pumps 4.1 to 4.4 (not shown) and the monitors 18.1 to 18.4 are located on a respective plane in which the corresponding alignment 14.1 to 14.4 and the corresponding substantially vertically oriented ergonomical radius 20.1 to 20.4 are located.

Figure 4:
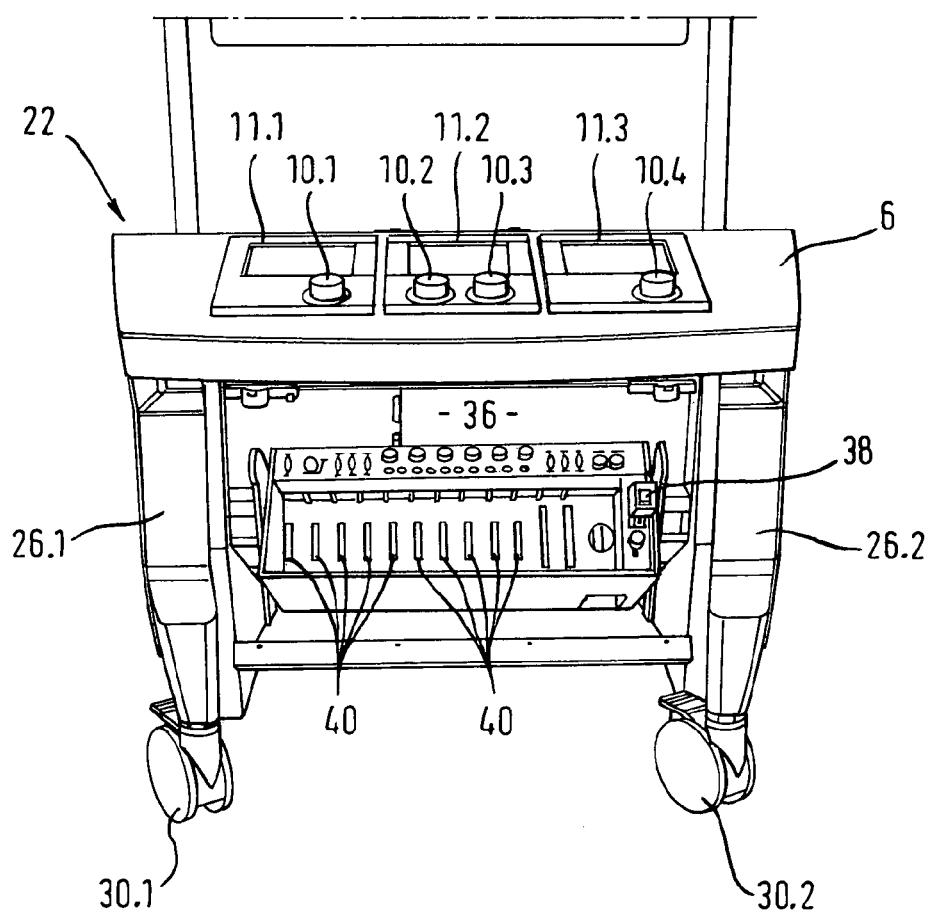
FIG. 4 shows a medical device aggregate in a front perspective view.

FIG. 4 shows a medical device aggregate 22, which in this case also forms a heart-lung machine. The medical device aggregate 22 comprises two lateral parts 26.1 and 26.2 which are flat and horizontally distanced so as to define a space 36 between them. The lateral members 26.1, 26.2 are supported on four rollers, of which FIG. 4 shows only rollers 30.1 and 30.2 of the front side of the medical device aggregate. Not shown in FIG. 4 is a connection member 28 that connects the two lateral parts 26.1, 26.2 so that they are distanced from each other and connected in a dimensionally stable manner. In the preferred embodiment described here, the connection member 28 and the lateral parts 26.1, 26.2 are made from die cast aluminium and may also be designed in one piece as torsion frame. In the embodiment shown here, the connection member 28 is provided only at an upper edge of the lateral members 26.1, 26.2, but a further connection member connecting the lower edges of the lateral members 26.1, 26.2 with each other may also be provided. In this case, a closed torsion frame is created, which is distinguished by a particularly high strength.

A plug-in device 48 having a plurality of slots 40 for plug-in boards or the like is accommodated in the space 36 between the lateral members 26.1, 26.2. The plug-in device 38 is installed within the space 36 between the lateral members 26.1, 26.2 in an oblique orientation with respect to a horizontal plane in order to allow easy insertion of plug-in boards into the slots 40 and use the space 36 between the lateral members 26.1, 26.2 efficiently.

In analogy to FIGS. 1 to 3, FIG. 4 shows a control panel 6 above the space 36, which comprises four control elements 10.1 to 10.4. The four control elements 10.1 to 10.4 are accommodated in three control modules 11.1 to 11.3. The middle control module 11.2 comprises two control elements 10.2 and 10.3 thus facilitating a space-saving arrangement of the control elements 10.1 to 10.4. The control elements 10.1 to 10.4 may, however, also be inserted into the control panel 6 as single modules. Each of the control modules 11.1 to 11.3 is inserted into the control panel 6, thus making it possible to easily remove one or more control modules 11.1 to 11.3 and, consequently, the corresponding control elements 10.1 to 10.4 from the control panel 6 or to replace them. This makes it possible to easily reconfigure the device aggregate, and additionally reduces the effort for possible maintenance work since the individual modules are replaceable, the device thus being immediately ready for use again, and the module to be serviced or repaired can be worked on at an appropriate location using extensive technical possibilities. Of course, modules other than the control modules 11.1 to 11.3 shown here may also be inserted into the control panel 6.

The interfaces of the control elements 10.1 to 10.4 and of other devices contained in the medical device aggregate 22 may preferably be reached from space 36 where they can be connected by means of cables and/or hose connections in a upper region between the lateral members 26.1, 26.2. The cables and/or hose connections (not shown) preferably run in an upper region of the space 36 and are connected to the plug-in device 38 as necessary.

The features mentioned for the control elements 10.1 to 10.4 and their modules 11.1 to 11.3 are analogously applicable to the medical devices such as pumps present in the medical device aggregate 22. Altogether, the medical device aggregate 22 described herein has a modular structure, and thus individual modules may be present in the device aggregate 22 almost without restrictions and may be exchanged for each other.

FIG. 5 shows a three-dimensional sectional view of the medical device aggregate 22 described in FIG. 4. Apart from the elements already described, FIG. 5 shows a front and a rear cover 32.1, 32.2, wherein the front cover 32.2 further comprises an openable flap 34, shown in FIG. 5 in its open position.

The openable flap 34 may be swung open downwards around a horizontally oriented axis of rotation, precisely around a hinge 33 disposed at the lower rim of the flap 34. The openable flap 34 has the advantage to provide, in its open state, easy access to the interior of the space 36 present between the lateral members 26.1, 26.2 and the connection member 28 between the lateral members 26.1, 26.2.

The plug-in device 38 already shown in FIG. 4 and further peripheral devices, electronics or a battery for power supply may be accommodated within the space 36. When flap 34 is closed, these components of the device aggregate 22 are accommodated and protected within the space 36 by the lateral members 26.1, 26.2, the cover 32.1, 32.2, the connection member 28 and a floor part 35, and they may nevertheless be quickly and comfortably reached by simply opening the flap 34. In particular, this is of special advantage for purposes of maintenance.

An important component of a mobile medical device aggregate 22, which is to be serviced rather often, is the preferably rechargeable battery which in most cases ensures the power supply of the medical devices of the aggregate. The capacity of the battery decreases with service life and, thus, may become an important risk factor. To prevent this, the battery is already checked at the first indication of aging or also at regular intervals, and is substituted as needed. In order to simplify and accelerate as much as possible this maintenance operation as well as other maintenance work such as checking hose lines or replacing electronic components, the openable flap 34 provides disassembly-free access to the space 36 in the interior of the torsion frame that consists of lateral parts 26.1, 26.2 and connection 28.

FIG. 5 shows a view of the device aggregate 22 in which a medical device 24 in form of a pump is shown beside the control elements 10.3, 10.4. As already described above, the pump can be inserted into the device aggregate 22, replaced and also removed therefrom in a modular manner. In analogy to the figures described above, two monitors 18.3, 18.4 embedded in a display panel 16 are located above the pump. The display panel 16 is in turn mounted to a pole 17.2 that is part of a pole system 17.

FIG. 6 shows a side view of the medical device aggregate that was already shown in FIGS. 4 and 5. Additionally, the side view illustrated in FIG. 6 shows a sectional view of the medical device aggregate 22. FIG. 6 shows the connection member 28 extending between the lateral members 26.1, 26.2 and connecting them to each other in a dimensionally stable manner. The connection member 28 and lateral members 26.1, 26.2, and possibly a further connection member that might for example be fixed at a lower rim of the lateral members 26.1, 26.2, may also be designed in one piece.

At the same time, as can be easily be taken from FIG. 6, the connection member 28 serves to accommodate one or more medical devices, of which only one medical device 24 is shown here and which is constituted by a medical pump just like in the above-described figures.

Apart from the space 36 shown in FIG. 6 and the plug-in device 38 disposed therein and installed, as described, in an oblique orientation, FIG. 6 shows the front and rear cover 32.1, 32.2, wherein the front cover 32.2 further comprises an openable flap 34. The flap 34 can be swung open around hinge 33 as shown in FIG. 5, but is shown in its closed position in FIG. 6. In addition to FIG. 4 and FIG. 5, FIG. 6 shows a further roller 30.3 upon which the lateral member 26.2 is supported. Analogously, the lateral member 26.1 is supported on two rollers, too.

The invention claimed is:
1. A life support system comprising:
a plurality of medical devices including at least a first medical device, a second medical device and a third medical device;
a control panel including at least a first control element, a second control element and a third control element, each of the control elements associated with one of the plurality of medical devices, each of the control elements for operating the associated one of the plurality of medical devices;
a designated control position; and
a display panel including at least a first display and/or monitoring element, a second display and/or monitoring element, and a third display and/or monitoring element, each display and/or monitoring element associated with one of the plurality of medical devices, each display and/or monitoring element displaying and/or monitoring system and/or operating conditions of an associated medical device;

wherein the control panel is configured such that the first medical device, the first control element and the first display and/or monitoring device are arranged along a first alignment line, the second medical device, the second control element and the second display and/or monitoring device are arranged along a second alignment line, and the third medical device, the third control element and the third display and/or monitoring device are arranged along a third alignment line, where each of the first alignment line, the second alignment line and the third alignment line extend to the designated control position, and wherein the first, second, and third display and/or monitoring elements are positioned at a first polar angle $\theta_1$ and visible from a point of observation at the designated control position, the first, second, and third medical devices are positioned at a second polar angle $\theta 2$ that is greater than the first polar angle $\theta_1$ and visible from the point of observation at the designated control position, and the first, second, and third control elements are positioned at a third polar angle $\theta 3$ that is greater than the second polar angle $\theta 2$ and visible from the point of observation at the designated control position.

2. The life support system of claim 1, wherein the display and/or monitoring elements are fixedly incorporated into the display panel.

3. The life support system of claim 1, wherein the control elements are arranged next to each other on the control panel.

4. The life support system of claim 3, wherein the control elements are horizontally aligned with the designated control position.

5. The life support system of claim 1, wherein horizontal alignments of each of the control elements and the associated medical devices converge at the designated control position.

6. The life support system of claim 1, wherein the control elements are arranged in a specifiable spacing interval from the designated control position.

7. The life support system of claim 1, wherein the display and/or monitoring elements are each arranged above the control elements, with respect to the designated control position.

8. The life support system of claim 1, wherein one of the control elements, one of the plurality of medical devices and one of the display and/or monitoring elements are respectively arranged on an ergonomic radius.

9. The life support system of claim 1, wherein the control panel protrudes over a base area of the plurality of medical devices above knee height of an operator sitting at the control position, a distance of the control elements to the designated control position is within reach of the operator, and the display and/or monitoring elements are positionable at eye level of the operator.

10. The life support system of claim 1, comprising a heart lung machine.

11. A heart lung machine comprising:
a plurality of pumps including at least a first pump and a second pump;
a control panel including at least a first control element and a second control element, each of the separate control elements associated with one of the plurality of pumps, each of the separate control elements for operating the associated one of the plurality of pumps;
a designated control position; and
a display panel including at least a first display element and a second display element, each display element associated with one of the plurality of pumps, each display element displaying system and/or operating conditions of an associated pump;
wherein the control panel is configured such that the first pump, the first control element and the first display element are arranged along a first alignment line with the first pump disposed in an open space between the first control element and the first display element, and
the second pump, the second control element and the second display element are arranged along a second alignment line with the second pump disposed in an open space between the second control element and the second display element,
wherein each of the first alignment line and the second alignment line extend to the designated control position.

12. The heart lung machine of claim 11, wherein the display elements are fixedly incorporated into the display panel.

13. The heart lung machine of claim 11, wherein the control elements are arranged next to each other on the control panel.

14. The heart lung machine of claim 13, wherein the control elements are horizontally aligned with the designated control position.

15. The heart lung machine of claim 11, wherein horizontal alignments of each of the control elements and the associated pumps converge at the designated control position.

16. The heart lung machine of claim 11, wherein the control elements are arranged in a specifiable spacing interval from the designated control position.

17. The heart lung machine of claim 11, wherein the display elements are each arranged above the control elements with respect to the designated control position.

18. The heart lung machine of claim 11, wherein the display elements, each of the plurality of pumps and the control elements are arranged in this order at successive polar angles ($\theta_1$ to $\theta_2$), as seen from the designated control position.

* * * * *